US010245234B1

(12) United States Patent
Lele (10) Patent No.: US 10,245,234 B1
(45) Date of Patent: Apr. 2, 2019

(54) METHOD OF TREATING CANCER WITH EDIBLE OIL DERIVED EXCIPIENTS

(71) Applicant: Bhalchandra Shripad Lele, Wilmington, DE (US)

(72) Inventor: Bhalchandra Shripad Lele, Wilmington, DE (US)

( * ) Notice: Subject to any disclaimer, the term of this patent is extended or adjusted under 35 U.S.C. 154(b) by 0 days.

(21) Appl. No.: 15/859,561

(22) Filed: Dec. 31, 2017

(51) Int. Cl.
| | |
|---|---|
| A61M 37/00 | (2006.01) |
| A61K 9/51 | (2006.01) |
| A61P 35/00 | (2006.01) |
| A61K 31/337 | (2006.01) |
| A61K 9/00 | (2006.01) |

(52) U.S. Cl.
CPC .......... *A61K 9/5123* (2013.01); *A61K 9/0019* (2013.01); *A61K 9/5138* (2013.01); *A61K 9/5146* (2013.01); *A61K 31/337* (2013.01); *A61P 35/00* (2018.01)

(58) Field of Classification Search
CPC .. A61K 9/5123; A61K 9/0019; A61K 31/337; A61P 35/00; A61M 37/0015; B29C 39/025; B29C 39/123; B29C 41/22; B29C 41/34
See application file for complete search history.

(56) References Cited

U.S. PATENT DOCUMENTS 9,085,709 B1 * 7/2015 Lele ..................... C09D 163/10

OTHER PUBLICATIONS

Sparreboom et al, Clin Cancer Res 2005; 11:4136-4143 (Year: 2005).*
Crosasso et al, Preparation, Characterization and Properties of Sterically Stabilized Paclitaxel-Containing Liposomes, Journal of Controlled Release 63, (2000), 19-20.*
Sparreboom A. et al, Comparative Preclinical and Clinical Pharmacokinetics of a Cremophor Free, Nanoparticle Albumin Bound Paclitaxel (ABI-007) and Paclitaxel Formulated in Cremophor (Taxol). Clin. Cancer Res. 2005, 11, 4136-4143.
Rugo H. et al, Randomized Phase III Trail of Paclitaxel Once Per Week Compared With Nanoparticle Albumin Bound Nab-Paclitaxel Once Per week or Ixabepilone With Bevacizumab as First Line Chemotherapy for Locally Recurrent or Metastatic Breast Cancer: CALGB 40502/NCCTG N063H (Alliance). J. Clin. Oncology 2015, 33, 2361-2369.
Szebini J. et al. Complement Activation by Cremophor EL as a Possible Contributor to Hypersensitivity to Paclitaxel: an In Vitro Study. J. Natl. Cancer Inst. 1998, 90, 300-306.
Bantchev G. et al. Free Radical Addition of Butanethiol to Vegetable Oil Double Bonds. J. Agric. Food Chem. 2009, 57, 1282-1290.

* cited by examiner

Primary Examiner — Carlos A Azpuru (57) ABSTRACT

Present invention teaches an improved method of treating cancer comprising intravenously administering to a subject in need thereof substantially ethanol free nanoparticles comprising an anticancer drug and a substantially hydroxyl free unsaturated edible oil saturated at least at one site of unsaturation by a covalently attached hydrogen atom and a covalently attached water soluble polymer.

1 Claim, 9 Drawing Sheets

FIG. 1

Nanoparticle formed by PEGylated olive oil

Nanoparticle formed by Paclitaxel: PEGylated olive oil

METHOD OF TREATING CANCER WITH EDIBLE OIL DERIVED EXCIPIENTS

BACKGROUND OF THE INVENTION

Field of the Invention

Since the FDA approval of cancer drug Taxol, more man two decades of research activities have focused on providing safer methods of treating cancer using alternatives to Cremophor EL (polyoxyethylated castor oil), the excipient used in formulating the active drug molecule, paclitaxel. Cremophor EL in Taxol (paclitaxel) is known to cause severe hypersensitivity reactions and dose limiting toxicities that are currently managed by antihistamine premedication and careful, in-hospital infusion of the drug. The research in methods of treating cancer with paclitaxel using alternatives to Cremophor EL have added many new materials in chemist's tool box including block copolymers, polymer prodrugs, vitamin E derivatives, protein carriers, chemically modified biopolymers, and crosslinked polymer particulates. Essentially, all such methods of treating cancer avoid or circumvent the original problem by administering paclitaxel formulated in a completely different drug carrier substance rather than solving the problem by administering paclitaxel formulated in an excipient designed from safer edible oil as opposed to castor oil which is used in Cremophor EL.

Background Art of the Invention

Research in methods of treating cancer using alternatives to Cremophor EL did provide Taxol alternatives like Abraxane (human serum albumin and paclitaxel formulation) that mostly eliminated hypersensitive side effects associated with Cremophor EL. However, this benefit came at significantly higher cost and at higher incidences of peripheral neuropathy, nausea, vomiting and diarrhea than that observed with Taxol. Also, as active drug was same in both Taxol and Abraxane i.e. paclitaxel, the Abraxane formulation was found to provide no significant survival benefit over Taxol in breast cancer treatment (Sparreboom A. et al Clin Cancer Res 2005; 11:4136-4143). A phase III trial studying metastatic breast cancer treatment showed higher survival rate for Taxol arm than that observed for Abraxane arm of the study (Rugo, H. et al 2012, ASCO Annual Meeting Abstract No. CRA1002, "Randomized phase III trial of weekly paclitaxel (P) compared to weekly nanoparticle albumin bound nab-paclitaxel (NP) or ixabepilone (Ix) with or without bevacizumab (B) as first-line therapy for locally recurrent or metastatic breast cancer (MBC): CALGB 40502/NCCTG N063H (Alliance)"). It is therefore worthwhile to focus our efforts in solving the original problem as described above, by providing an improved method of treating cancer wherein paclitaxel is administered formulated in an excipient designed from safer edible oil as opposed to castor oil. Such an improved method of treating cancer will have significant pharmacoeconomic advantages for the cancer patients and their payers.

First limitation in providing said improved method of treating cancer wherein paclitaxel is administered formulated in an excipient designed from safer oil edible oil as opposed to castor oil, is the unique structural difference between castor oil and other safer edible oils. Castor oil has free hydroxyl groups in its structure in the center of fatty acid alkyl chains of the triglyceride ricinoleates. During the formation of Cremophor EL by reaction between castor oil and ethylene oxide, some of the free hydroxyls in castor oil react with ethylene oxide and form polyoxyethylated castor oil (Cremophor EL). Other safer edible oils do not have such natural free hydroxyl groups in their fatty acid alkyl chains structures to modify.

Also, there are transesterification reactions between ricinoleates and polyoxyethylene chains during formation of Cremophor EL. As a result, Cremophor EL, is a complex mixture of excipient/surfactant species wherein several hydroxyl groups in castor oil remain free i.e. unconsumed. The unreacted hydroxyl groups of castor oil moiety in Cremophor EL are implicated in complement activation which causes allergic/hypersensitivity reactions observed in patients (Szebeni, J., Muggia, F. M., Alving, C. R., J. Natl. Cancer Institute 90(4), 300-306 (1998) Complement activation by Cremophor EL as a possible contributor to hypersensitivity to paclitaxel: An in vitro study).

As such, excipients/surfactants that have naturally or synthetically created free hydroxyl groups in oil structures are not ideal for eliminating hypersensitivity reactions. For example, U.S. Pat. No. 9,085,709B1 describes preparation of epoxidized oil based surfactants wherein polyoxyethylene chains are attached in the center of fatty acid alkyl chains similar to those in Cremophor EL. However, free hydroxyl groups are inherently created in the oil structure as the epoxide rings are opened by the reaction of the epoxidized oil with the linker-polymer.

Lastly, oil based excipients such as Cremophor EL and Polysorbate 80 (used in Docetaxel formulation) require ethanol as cosolvent to obtain stable, usable formulations. Epoxidized soybean oil derived surfactants/excipients disclosed in U.S. Pat. No. 9,085,709B1 also use ethanol as cosolvent to obtain stable paclitaxel formulation. Taxane formulations containing significant amounts of ethanol can cause ethanol induced intoxication in patients. It is therefore neither known nor obvious from the prior art and/or to persons skilled in the art, an improved method of treating cancer comprising administering a substantially ethanol free taxane formulation in a substantially hydroxyl free edible oil based excipient that is safer substitute to Cremophor EL. It is also not obvious to persons skilled in the art that such a method of treating cancer can produce a substantially higher antitumor effect on an equitoxic basis, compared to existing paclitaxel formulations in Cremophor EL.

OBJECT OF THE INVENTION

Therefore the object of the present invention is to provide an improved method of treating cancer comprising administering to a subject in need thereof a substantially ethanol free taxane formulation in a substantially hydroxyl free edible oil based excipient that is safer substitute to Cremophor EL.

BRIEF SUMMARY OF THE INVENTION

The present invention discloses an improved method of treating cancer wherein a substantially ethanol free nanoparticle composition consisting an anticancer drug and a substantially hydroxyl five unsaturated oil saturated at least at one site of unsaturation by a covalently attached hydrogen atom and a covalently attached water soluble polymer is administered to a subject in need thereof. Compared to the current methods of treating cancer using toxic excipients and ethanol, the present method of treating cancer is shown to produce substantially higher antitumor effects at equitoxic dose without hypersensitivity reactions.

BRIEF DESCRIPTION OF TABLES

Table 1: Stability of substantially ethanol free paclitaxel: PEGylated olive oil formulations with different paclitaxel loadings.

Table 2: Comparison of hypersensitivity effects for Taxol treatment and treatment using substantially ethanol free nanoparticles comprising paclitaxel: PEGylated olive oil.

DETAILED DESCRIPTION OF THE INVENTION

Embodiments of the Invention

Figure 1:
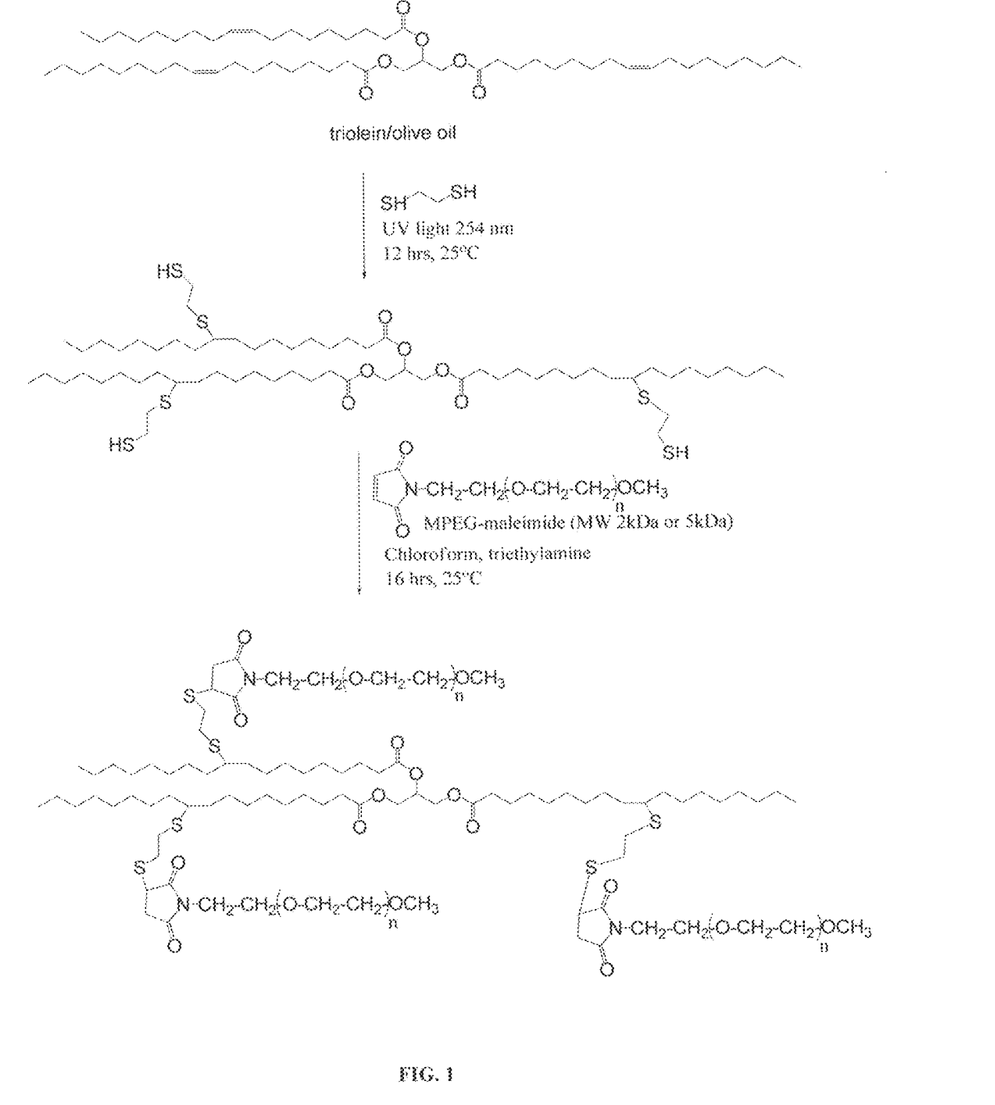
FIG. 1: Schematic representation of synthesis of PEGylated triolein/PEGylated olive oil as safer substitute excipient to Cremophor EL.

In an embodiment of the present invention, the present method of treating cancer makes use of unsaturated edible oils that do not contain free hydroxyl groups in their fatty acid alkyl chains (referred to as substantially hydroxyl free hereinafter); and are saturated at least at one site of unsaturation by a covalently attached hydrogen atom and u covalently attached water soluble polymer. Substantially hydroxyl free unsaturated edible oils saturated at least at one site of unsaturation by a covalently attached hydrogen atom and a covalently attached water soluble polymer used in present method of treating cancer are prepared as follows: for example, triolein or olive oil (which is >80% triolein) saturated at least at one site Of unsaturation by a covalently attached hydrogen atom and a covalently attached water soluble polymer is prepared by thiol-ene free radical addition reaction of triolein or olive oil with an excess of dithiol such as for example 1.2-ethanedithiol to saturate the unsaturation sites i.e. carbon-carbon double bond(s) in the respective oil with one hydrogen atom and one —S—$CH_2$—$CH_2$—SH group each. Subsequently, a thiol reactive water soluble polymer such as for example methoxy-polyethylene glycol$_{2000}$-maleimide is conjugated to the thiol groups introduced in the modified oil. Unlike hydroxyls, thiols are very reactive and quantitatively consumed by thiol reactive groups such as maleimide. The conjugate of modified triolein or olive oil with polyethylene glycol synthesized as above or via alternate chemistries (described in the following) is termed as PEGylated triolein and PEGylated olive oil, respectively hereinafter. FIG. 1 schematically represents synthesis of PEGylated triolein or PEGylated olive oil as safer substitute to Cremophor EL.

Thiol-ene free radical addition chemistry of unsaturated oils are known in the prior arts (Bantchev, G. B., Kenar, J. A., Biresaw, G., Han. M. G. J. Agric. Food Chem. 2009; 57: 1282-1290) however, it is neither known nor obvious from these prior arts that a safer substitute excipient to Cremophor EL can be prepared and used in an improved method to treat cancer as disclosed here. Due to general applicability of thiol-ene free radical addition chemistry to unsaturated oils it will be recognized by persons skilled in the art that the scope of the present invention is not limited to use of only triolein/olive oil as substantially hydroxyl free unsaturated oil and 1,2-ethanediol as unsaturated oil modifier thiol. Similarly, due to general applicability of conjugation reaction between thiol and thiol reactive linker it will be recognized by persons skilled in the art that the scope of the present invention is not limited to use of only polyethylene glycol as water soluble polymer and maleimide as reactive linker between thiol modified oil and water soluble polymer. Several other known hydroxyl free unsaturated oils, dithiols, thiol reactive linkers; and water soluble polymers are anticipated to tall within the scope of the present invention when following the improved method of treating cancer disclosed here.

Thus, in another embodiment, the method of treating cancer disclosed in present invention makes use of a variety of substantially hydroxyl free unsaturated edible oils selected from a group comprising olive oil, corn oil, canola oil, soybean oil, rapeseed oil, linseed oil, trilinolein, triolein, peanut oil, sunflower oil, mustard oil, almond oil, palm oil, sesame oil, safflower oil, cottonseed oil, grape seed oil, rice bran oil, mono, di, triglycerides of unsaturated fatty acids of C7 to C22 chain length, unsaturated fatty acids of C7 to C22 chain length, and mixtures thereof; and saturates them at least at one site of unsaturation by a covalently attached hydrogen atom and a covalently attached water soluble polymer as described above.

In an another embodiment, the method of treating cancer disclosed in present invention makes use of a variety of substantially biocompatible water soluble polymers selected from a group comprising polyethylene glycol, polyethylene oxide, polyethylene glycol methyl ether, homo and heterobifunctional polyethylene glycols, polyethylene glycol-co-polypropylene glycol, polyethylene oxide-block-polypropylene oxide, polyethylene glycol-acrylate, polyethylene glycol-methacrylate, monomethoxypolyethylene glycol-acrylate, monomethoxypolyethylene glycol-methacrylate, poly(N-2-hydroxypropylmethacrylamide), poly(N-vinylpyrrolidone), poly(N-isopropylacrylamide), poly(acrylic acid), poly(methacrylic acid), poly(2-aminoethyl methacrylate), poly(N,N-dimethylaminoethyl methacrylate), poly(2-methacryloyloxyethylphosphorylcholine), poly(methoxypolyethylene glycol-methacrylate), poly(methoxypolyethylene glycol-acrylate) and combinations thereof; to covalently attach to said substantially hydroxyl free unsaturated oils.

In another embodiment, the method of treating cancer disclosed in the present invention makes use of a variety of dithiols selected from a group comprising 1,2-ethanedithiol, 1,3-propanedithiol, 1-4-butanedithiol, 1,6-hexanedithiol, 2,2'-(ethylenedioxy)diethanedithiol and the likes; to saturate at least one site of unsaturation in said substantially hydroxyl free unsaturated oils via thiol-ene free radical addition reaction of the said oil and the excess of the said dithiol and obtain said thiol modified oils.

In an another embodiment, the method of treating cancer disclosed in the present invention makes use of a variety of thiol reactive tinkers containing functionalities selected from a group comprising maleimide, acrylate, methacrylate, isocyanate, isothiocyanate, iodoacetamido, bromoacetamide, thioether, and the likes; to covalently link said water soluble polymers and said thiol modified oils.

Figure 2:
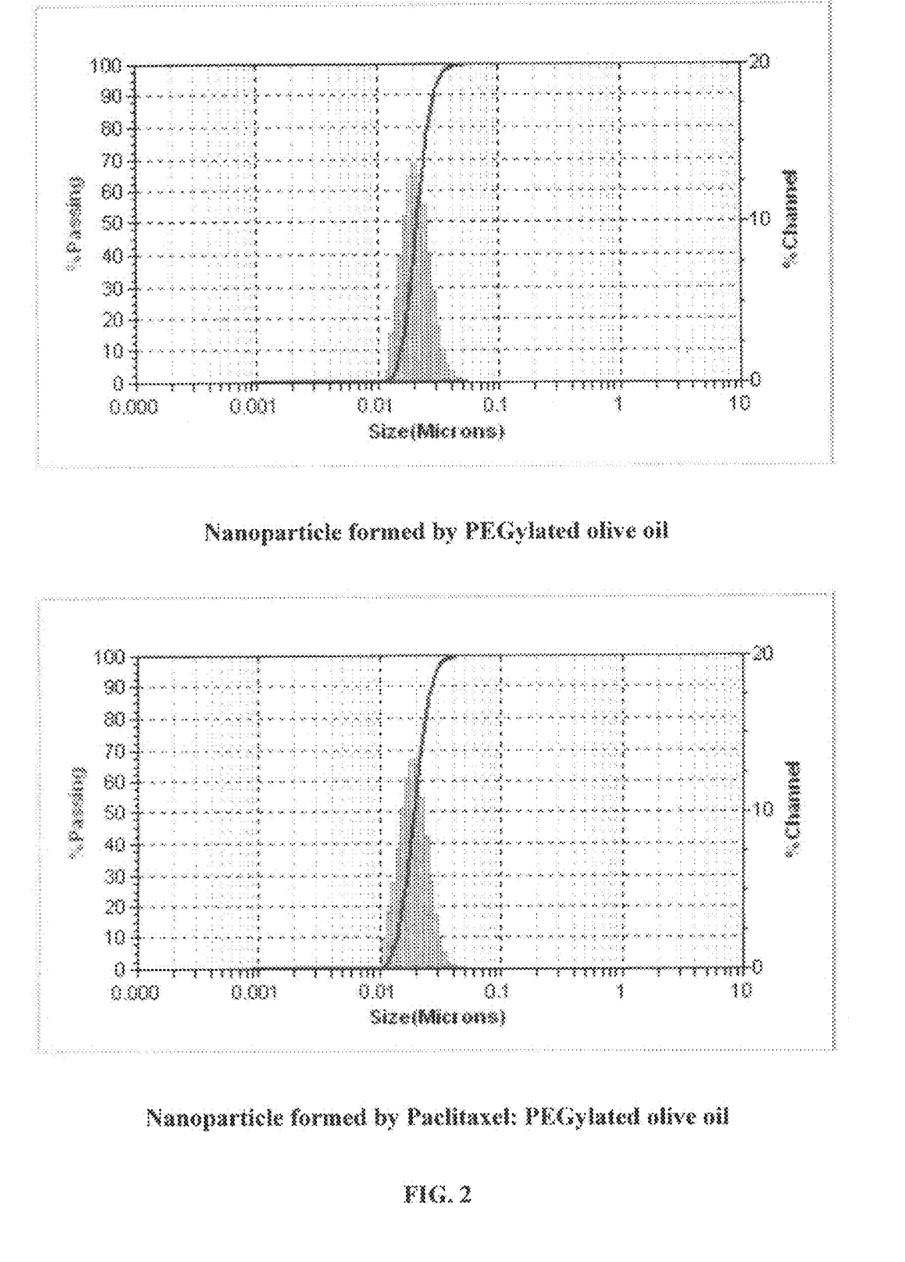
FIG. 2: Particle size characterization of substantially ethanol free nanoparticles comprising PEGylated olive oil, and paclitaxel; PEGylated olive oil respectively, by dynamic light scattering.

In yet another embodiment of the present invention, the present method of treating cancer makes use of substantially ethanol free nanoparticles comprising a taxane and a substantially hydroxyl free unsaturated edible oil saturated at least at one site of unsaturation by a covalently attached hydrogen atom and a covalently attached water soluble polymer. For example, paclitaxel and PEGylated olive oil, prepared as described earlier, are first completely dissolved in ethanol followed by evaporating the ethanol under vacuum. The residue is dissolved in a saline solution (0.9% sodium chloride in water) or a dextrose solution (5% dextrose in water) to obtain a visibly clear aqueous solution containing self-assembled nanoparticles which is filtered and lyophilized to obtain the dry powder. The lyophilized powder is reconstituted in water to obtain a visibly clear solution containing substantially ethanol free nanoparticles comprising paclitaxel and olive oil saturated at least at one site of unsaturation by covalently attached hydrogen atom and covalently attached water soluble polymer of the formula —S—$CH_2$—$CH_2$S—maleimido-polyethylene glycol$_{2000}$-methoxy. Said substantially ethanol free nanoparticles are highly uniform in size as shown in FIG. 2 with hydrodynamic diameter of 25-40 nm. However, it is to be understood by persons skilled in the art that hydrodynamic diameter of said substantially ethanol free nanoparticles of the present invention can be in the range of 10 nm to 200 nm.

In an another embodiment of the present invention, the present method of treating cancer makes use of said substantially ethanol free nanoparticles comprising around 1-10 percent by weight of a taxane and around 90-99 percent by weight of a substantially hydroxyl free unsaturated edible oil saturated at least at one site of unsaturation by a covalently attached hydrogen atom and a covalently attached water soluble polymer. For example, as shown in Table 1, the present method of treating cancer can make use of substantially ethanol free nanoparticles comprising different loadings of paclitaxel formulated in PEGylated olive oil. As shown in Table 1 said substantially ethanol free nanoparticles containing different loadings of a taxane (paclitaxel) are stable over a range of practically useful time periods. To persons skilled in the art, it is unexpected result that an oil based excipient is providing substantially ethanol free, stable taxane formulations.

In yet another embodiment of the present invention, present method of treating cancer intravenously administers, to a subject in need thereof, said substantially ethanol free nanoparticles comprising around 1-10 percent by weight of a taxane and around 90-99 percent by weight of a substantially hydroxyl free unsaturated edible oil saturated at least at one site of unsaturation by a covalently attached hydrogen atom and a covalently attached water soluble polymer. For example, female Swiss Webster (SW) mice in which MDA-MB-231 human breast cancer tumors are established, are intravenously given therapeutically effective amount of substantially ethanol free nanoparticle composition wherein nanoparticle composition comprises nanoparticles having hydrodynamic diameter of about 25-40 nm comprising about 1 percent by weight of paclitaxel and about 99 percent by weight of olive oil saturated at least at one site of unsaturation by covalently attached hydrogen atom and covalently attached water soluble polymer of formula —S—$CH_2$—$CH_2$S—maleimido-polyethylene glycol$_{2000}$-methoxy.

In yet another embodiment of the present invention, present method of treating cancer is substantially free from inducing hypersensitivity reactions. For example, as shown in Table 2, no hypersensitivity reactions such as hunched posture, wheezing, lethargy, shortness of breath were observed in female SW mice having MDA-MB-231 tumors, and treated with therapeutically effective amount of substantially ethanol free nanoparticles having hydrodynamic diameter of about 25-40 nm comprising about 1 percent by weight of paclitaxel and about 99 percent by weight of olive oil saturated at least at one site of unsaturation by covalently attached hydrogen atom and covalently attached water soluble polymer of formula —S—$CH_2$—$CH_2$S—maleimido-polyethylene glycol$_{2000}$-methoxy. On the contrary, hypersensitivity reactions such as hunched posture, wheezing, shortness of breath, lethargy were clearly observed in female SW mice having MDA-MB-231 tumors, and treated with therapeutically effective amount of Taxol.

In yet another embodiment, present method of treating cancer produces substantially higher antitumor effects compared to conventional method of treating cancer with Taxol, on an equitoxic basis. For example, in repeated dosing, maximum tolerated dose (MTD) of Taxol was found to be 15 mg/Kg (of paclitaxel) in female SW mice. On the contrary, in repeated dosing, MTD was 30 mg/Kg (of paclitaxel) in female SW mice for substantially ethanol free nanoparticles comprising about 1 percent by weight of paclitaxel and about 99 percent by weight of olive oil saturated at least at one site of unsaturation by covalently attached hydrogen atom and covalently attached water soluble polymer of formula —S—$CH_2$—$CH_2$S-maleimido-polyethylenc glycol$_{2000}$-methoxy. See FIG. 3 for results of maximum tolerated dose study of the present and conventional methods of treating cancer using paclitaxel. As present method of treating cancer was able to administer substantially higher amount of paclitaxel safely than that could be administered by conventional methods using Taxol. the present method of treating cancer produced substantially higher antitumor effects (higher tumor volume shrinkage) compared to the conventional method of treating cancer using Taxol. See FIG. 4 and FIG. 5 for comparison of body weight data and antitumor effects (tumor volume shrinkage) respectively, of the present and the conventional methods of treating cancer using paclitaxel.

Statistical analysis of this data was performed using one way ANOVA with Tukey HSD post hoc comparisons and $p<0.05$ was considered as statistically significant. There was statistically significant difference in tumor sizes between the paclitaxel: PEGylated olive oil group and the vehicle group ($p=0.0072$), whereas, the difference in tumor sizes between the vehicle group and the Taxol group was not statistically significant ($p=0.18$). Similarly, there was statistically significant difference in body weight of the paclitaxel: PEGylated olive oil group and the vehicle group ($p=0.010$) whereas, the difference in body weight of the Taxol group and the vehicle group was not statistically significant (p=0.15). Data clearly show the present method of treating cancer provides substantially improved results for tolerability, hypersensitivity and tumor size reduction than that provided by the conventional method using Taxol.

Persons skilled in the art will recognize that the scope of the present method of treating cancer is not limited to only treating breast cancer with taxanes. Various other cancers treatable by taxanes such as non-small cell lung cancer, ovarian cancer, head and neck cancer. Kaposi's sarcoma, pancreatic cancer are anticipated to fall within the scope of the present method of treating cancer. Similarly, although present method of treating cancer describes the use of taxanes as anticancer agents, persons skilled in the art will recognize that use of non-taxane anticancer agents such as doxorubicin, vinblastine, camptothecin, curcumin, retinoic acid, luteolin, melphalan, teniposide, etiposide, tanespimycin, irinotecan, SN38, rapamycin, cyclosporine, 17-AAG and the likes are anticipated to fall within the scope of the present invention.

Embodiments described above and Examples described in the following clearly convey to persons skilled in the art that the present disclosure teaches the stated objective of the invention i.e. an improved method of treating cancer comprising administering to a subject in need thereof a substantially ethanol free taxane formulation in a substantially hydroxyl free edible oil based excipient that is safer substitute to Cremophor EL. The present method of treating cancer is also shown to provide significantly higher antitumor effects compared to conventional method of treating cancer using Taxol, on an equitoxic basis.

Figure 6:
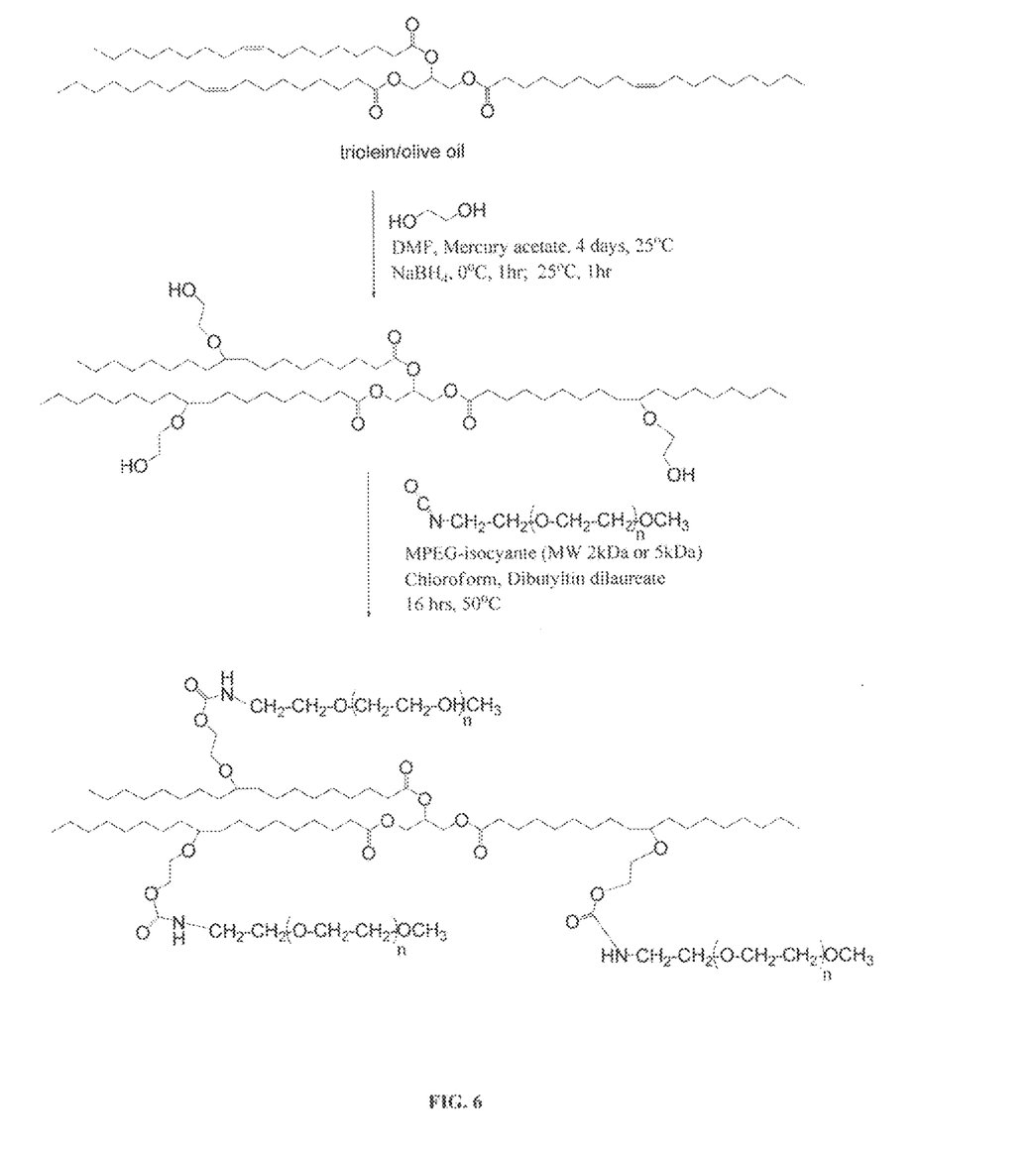
FIG. 6: Schematic representation of synthesis of PEGylated triolein/PEGylated olive oil as safer substitute excipient to Cremophor EL via alternate, oxymercuration-demercuration chemistry.

Examples below are illustrative and not limiting in nature in describing the scope of the present invention. Persons skilled in the art will recognize that several chemistries such as illustrated in Examples 12-16 and FIGS. 6-10 can be used to essentially arrive at substantially hydroxyl free unsaturated edible oils saturated at least at one site of unsaturation by a covalently attached hydrogen atom and a covalently attached water soluble polymer and used in treating cancer without deviating from the spirit of the present invention. For example, as illustrated in FIG. 6 and Example 12. PEGylated triolein/PEGylated olive oil useful in present method of treating cancer can be prepared by oxymercuration-demercuration reaction of triolein/olive oil with an excess of a diol such as 1,2-ethanediol to saturate double bond(s) in the oil with one hydrogen atom and one —O—CH$_2$—CH$_2$—O group each (F. D. Gunstone, R. P. Inglis, Chemistry and Physics of Lipids 1973; 10: 73-88). Subsequently, a hydroxyl reactive water soluble polymer such as for example methoxy-polyethylene glycol$_{2000}$-isocyanate can be conjugated to hydroxyl groups introduced in the modified oil. Also as shown in FIGS. 7-10 and Examples 13-16 different polymerization techniques to grow polymer chains from thiol or hydroxyl modified oils disclosed here can be used to arrive at substantially hydroxyl free unsaturated edible oils saturated at least at one site of unsaturation by a covalently attached hydrogen atom and covalently attached water soluble polymer and used in treating cancer as disclosed here.

EXAMPLES

Synthesis and formulation work was carried out as contract research at Pharmagra Labs, Brevard N.C. In vivo toxicity and antitumor efficacy studies were carried out as contract research at Washington Biotechnology Inc., Baltimore Md. Particle size analysis was earned out as contract research at Microtrac Inc. Largo; Fl. Endotoxin testing was done as contract research at Micromed Laboratories, Petaluma, Calif.

Example 1

Synthesis of Thiol Modified Triolein

Triolein (Sigma-Aldrich, 500 mg, 0.56 mmol) was taken in a glass vial. To this, 1,2-ethanedithiol (Sigma-Aldrich, 0.55 mL, 6.6. mmol) and 2,2,-dimethoxyphenyl acetophenone (Sigma-Aldrich, 29 mg, 0.11 mmol) were added. The mixture was mixed with a disposable Pasteur pipette and the vial was irradiated overnight through the walls with a hand-held ultraviolet lamp (UV$_{max}$=254 nm). Saturation of double bonds in triolein by addition of 1,2-ethanedithiol was continued by $^1$H NMR. The adduct of triolein-1,2-ethanedithiol (thiol modified triolein) was purified to remove excess of 1,2-ethanedithiol by loading reaction mixture on a C$_{18}$ plug (2 g) directly and eluting with water until all excess 1,2-ethanedithiol was removed. Thiol modified triolein free from polymerized byproducts (if any), was eluted using 9:1 dichloromethane: methanol (15 mL). The solvents were evaporated under reduced pressure to obtain 630 mg of clear, colorless oil. Unpolymerized state of thiol modified triolein was confirmed by 1H NMR spectroscopy.

$^1$H NMR (CDCl$_3$): 0.9 δ triplet (9H, terminal —CH$_3$ of alkyl chains), 1.2-1.6 δ multiplet (84H, —(CH$_2$—)$_7$—CHSR—(CH$_2$)$_7$—), 2.3 δ triplet (6H, —CH$_2$—COO—), 2.5-2.6 δ pentuplet (3H, —CH—C—S—CH$_2$—CH$_2$—SH), 2.7-2.8 δ multiplet (11H, —CH—C—S—CH$_2$—CH$_2$—SH), 4.2-4.4 δ doublet (4H, RO—CH$_2$-CH(OR)-CH$_2$OR of glycerol backbone), 5.2 δ multiplet (1H, RO—CH$_2$—CH(OR)—CH$_2$—OR of glycerol backbone). Obtained NMR data are in agreement with the structure of thiol modified triolein shown in FIG. 1.

Example 2

Conjugate of Thiol Modified Triolein and Polyethylene Glycol (PEGylated Triolein)

A 50 mL round bottom flask was charged with stir bar, thiol modified triolein (146 mg, 0.125 mmol) and chloroform (16 mL), and methoxy-polyethylene glycol$_{2000}$-maleimide (752 mg, 0.376 mmol, from CreativePEGworks, MW=2 kDa). The mixture was stirred to dissolve the solids. To this solution, triethylamine (0.17 mL, 1.25 mmol) was added and stirred overnight at room temperature. The solution was concentrated and placed under high vacuum to evaporate solvents and obtain PEGylated triolein as off-white solids with >95% yield. Structure of PEGylated triolein was confirmed by $^1$H NMR spectroscopy.

$^1$H NMR (CDCl$_3$): 0.8-0.9 δ triplet (terminal —CH$_3$ of alkyl chains, 9H), 1.2-1.6 δ multiplet ( —(CH$_2$—)$_7$—CHSR—(CH$_2$)$_7$—), 2.2-2.8 δ four multiplets (aliphatic methylene protons in fatty acid chains and linker), 3.4-3.8 δ three multiplets (oxyethylene protons in PEG chains. 536H), 4.1 and 4.3 δ multiplet (4H, RO—CH$_2$-CH(OR)-CH$_2$OR of glycerol backbone), 5.2 δ multiplet (1H, RO—CH$_2$—CH(OR)—CH$_2$—OR of glycerol backbone). Obtained NMR data is in agreement with the structure of PEGylated triolein shown in FIG. 1.

Example 3

Synthesis of Thiol Modified Olive Oil and PEGylated Olive Oil

Olive oil is a mixture of triglycerides, in which >80% are oleic triglycerides i.e. triolein and the rest is primarily saturated triglycerides which do not undergo double bond modification reactions such as thiol-ene addition and is removed during precipitation and purification. In the present invention, $^1$H NMR of the olive oil used (extra virgin olive oil, product of Spain, procured from local supermarket) was identical to triolein which mean it contained negligible to none of saturated triglycerides, therefore, the reaction of olive oil with 1,2-ethanedithiol and conjugation of thiol modified olive oil with methoxy-polyethylene glycol$_{2000}$-maleimide was carried out essentially as described above for triolein. Structure of thiol modified olive oil confirmed by $^1$H NMR spectroscopy.

Thiol modified olive oil $^1$H NMR (CDCl$_3$): 0.8-0.9 δ triplet (terminal —CH$_3$ of alkyl chains, 9H), 1.2-1.6 δ multiplet (—(CH$_2$)$_7$—CHSR—(CH$_2$)$_7$—), 2.2-2.8 δ four multiplets (aliphatic methylene protons in fatty acid chains and linker), 3.4-3.8 δ three multiplets (oxyethylene protons in PEG chains, 536H), 4.1 and 4.3 δ multiplet (4H, RO—CH$_2$-CH(OR)-CH$_2$OR of glycerol backbone), 5.2 δ multiplet (1H, RO—CH$_2$—CH(OR)—CH$_2$—OR of glycerol backbone).

PEGylated olive oil 1H NMR (CDCl$_3$): 0.8-0.9 δ triplet (terminal —CH$_3$ of alkyl chains, 9H), 1.2-1.6 δ multiplet (—(CH$_2$)$_7$—CHSR—(CH$_2$)$_7$—), 2.2-2.8 δ four multiplets (aliphatic methylene protons in fatty acid chains and linker), 3.4-3.8 δ three multiplets (oxyethylene protons in PEG chains, 502H). 4.1 and 4.3 δ multiplet (4H, RO—CH$_2$-CH(OR)-CH$_2$OR of glycerol backbone), 5.2 δ multiplet (1H, RO—CH$_2$—CH(OR)—CH$_2$—OR of glycerol backbone). $^1$H NMR spectra of thiol modified olive oil and PEGylated olive oil were similar to that of the thiol modified triolein and PEGylated triolein, respectively. because the olive oil used was predominantly consisting triolein. In the synthesized PEGylated olive oil, the observed ratio of terminal methyl groups in the olive oil and oxyethylene groups in the PEG was 9:502 which is very close to the theoretical ratio is 9:544 for a monodispersed PEG 2000 and olive oil containing 100% triolein. Since olive oil was predominantly triolein as confirmed by 1H NMR, obtained NMR data for both thiol modified olive oil and PEGylated olive oil are in agreement with their structures shown in FIG. 1.

Example 4

Formulation of Paclitaxel with PEGylated Triolein (Ethanol: Water Solution)

A 5.0 mL volumetric flask was charged with PEGylated triolein (417 mg), paclitaxel (LC Labs Inc., 5 mg) and ethanol (0.42 mL). The mixture was heated to dissolve forming syrup which was viscous but homogeneous. While still warm, 0.9% (w/v) sodium chloride solution in water was added, bringing the total volume to 5 mL (1 mg paclitaxel/mL of formulation). It was allowed to stand overnight (15 hrs), at which time there was still no precipitation of paclitaxel observed.

Example 5

Substantially Ethanol Free Formulation of Paclitaxel with PEGylated Olive Oil (Lyophilized Powder)

A 5.0 mL volumetric flask was charged with PEGylated olive oil (415 mg), paclitaxel (5 mg), and ethanol (0.42 mL). The mixture was heated to dissolve, forming syrup which was viscous but homogeneous. While still warm, 0.9% w/v sodium chloride solution in water was added to the ethanol solution, bringing the total volume to 5 mL. The solution was concentrated under reduced pressure to obtain hygroscopic residue which was dissolved in water (5 mL, 1 mg paclitaxel/mL of formulation), filtered through 0.2 micron syringe filter, and lyophilized to dry powder. No undissolved material was seen before the filtration.

Alternatively, PEGylated olive oil (4.15 g), paclitaxel (50 mg), and ethanol (4.2 mL) were dissolved completely to obtain clear solution Ethanol was evaporated under vacuum. The residue was dissolved in 0.9% sodium chloride in water to obtain clear solution. The solution was filtered through 0.2 micron syringe filter and lyophilized to obtain dry powder. No undissolved material was seen before the filtration.

Example 6

Substantially Ethanol Free Nanoparticles Containing Paclitaxel and PEGylated Olive Oil Lyophilized powder from EXAMPLE 5 was reconstituted by adding water to obtain around 1 mg/ml paclitaxel concentration. The visibly clear solution was analyzed by dynamic light scattering. The results of analysis showed highly uniform nanoparticles of hydrodynamic diameter of 25 nm to 40 nm are formed for PEGylated olive oil alone as well as for paclitaxel formulated in PEGylated olive oil. See FIG. 2.

Example 7

Different Loadings of Paclitaxel (w/w) in PEGylated Olive Oil (w/w)

Paclitaxel (1 to 3% w/w) and PEGylated olive oil (97 to 99% w/w) were dissolved in ethanol and the solvents were evaporated. The residue was dissolved in 0.9% sodium chloride solution to obtain visibly clear solutions. Time required for developing turbidity/precipitate in these solutions containing different w/w loading of paclitaxel was recorded which is shown in Table 1.

Example 8

Determination of Endotoxin Levels

PEGylated olive oil and paclitaxel formulation in PEGylated olive oil both were analyzed for endotoxin contamination via LAL test at a contract research laboratory. As shown below, the endotoxin levels in the formulation were below permissible ranged.

Pegylated olive oil—Observed: 0.0135 endotoxin unit; device; Allowable: <0.25 endotoxin unit/device.

Pegylated olive oil: paclitaxel nanoformulation—Observed; 0.039 endotoxin unit/device; Allowable: <0.25 endotoxin unit/device.

Example 9

In Vivo Studies (Determination of Maximum Ink-Rated Dose (MTD):

Paclitaxel: PEGylated Olive Oil Formulation

Fifteen female SW mice (from Taconic, weight 16-20 g) were randomly assigned in three groups of 5 each. The paclitaxel: PEGylated olive oil nanoformulation was reconstituted in water to 2 mg/ml paclitaxel cone. Then doses equivalent to 30, 40, and 50 mg/kg of paclitaxel were administered intravenously to mice in each group. Mice were monitored for about on hour after dosing to see if any hypersensitive reactions are exhibited. No signs of hypersensitive reaction such as shortness of breath, shivering, lack of movement, and hunched posture were observed that are typically observed with Taxol. See data in Table 2. Dosing was continued for next four consecutive days. Mice were monitored fix body weight measurements and general behavior for next 15 days. At the end of the study surviving mice were weighed, euthanized, and gross necropsy was performed. No abnormality was observed.

Taxol Formulation

Twenty female SW mice (from laconic, weight 16-20 g) were randomly assigned in four groups of 5 each. Taxol formulation was diluted to 2 mg/ml paclitaxel cone. Then, doses equivalent of 15, 30, 40, and 50 mg/kg of paclitaxel were administered intravenously to mice in each group. Mice were monitored for about an hour after dosing to see if any hypersensitive reactions are exhibited. Immediately after dosing, definitive signs of hypersensitive reaction were observed such as shortness of breath, shivering, lack of movement, and hunched posture. Mice recovered slowly in 6 hours post dosing. See Data in Table 2. Dosing was continued for next four consecutive cays. Mice were monitored for body weight measurements and general behavior for next 15 days. At the end of the study surviving mice were weighed, euthanized, and gross necropsy was performed. No abnormality was observed.

Example 10

Antitumor Activity of Taxol and Paclitaxel: PEGylated Olive Oil Formulations

Figure 3:
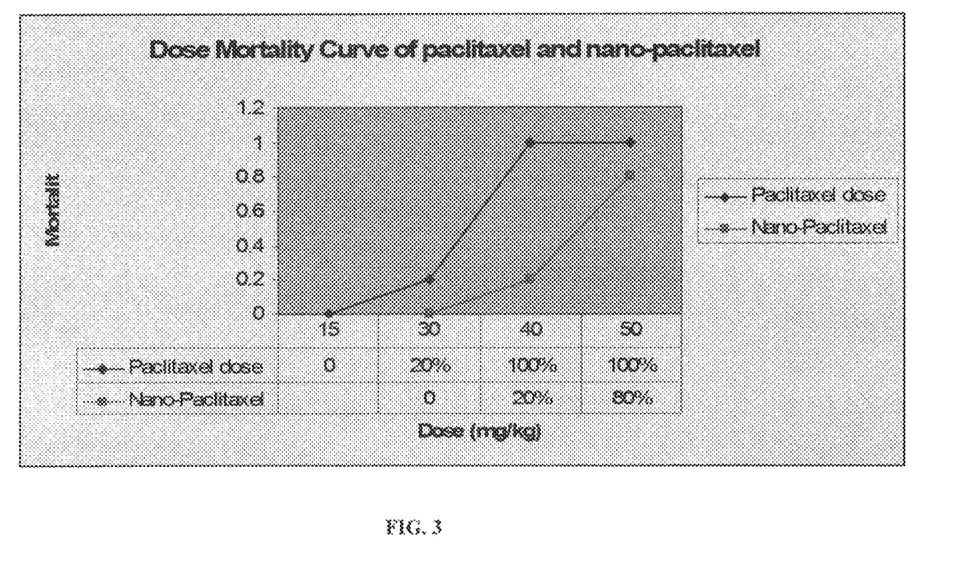
FIG. 3: Comparison of maximum tolerated dose of Taxol formulation and substantially ethanol free nanoparticles comprising paclitaxel: PEGylated olive oil.
Figure 4:
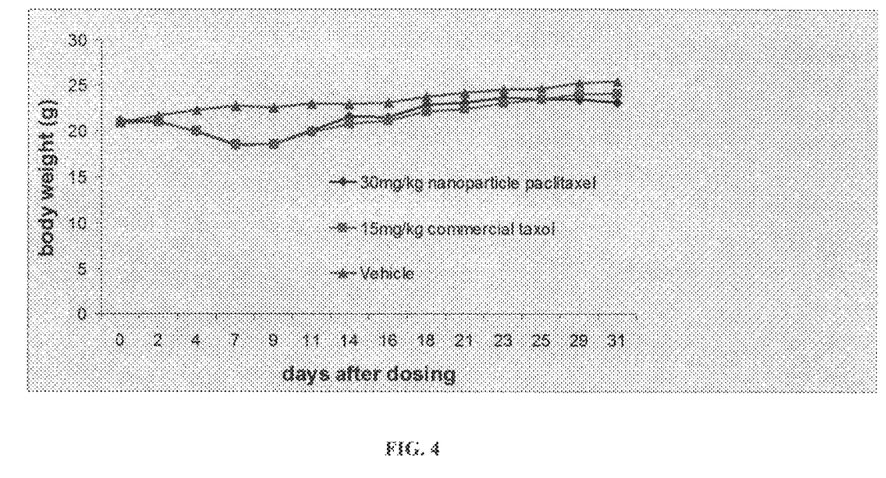
FIG. 4: Comparison of body weight data for Taxol treatment and the treatment using substantially ethanol free nanoparticles comprising paclitaxel: PEGylated olive oil.
Figure 5:
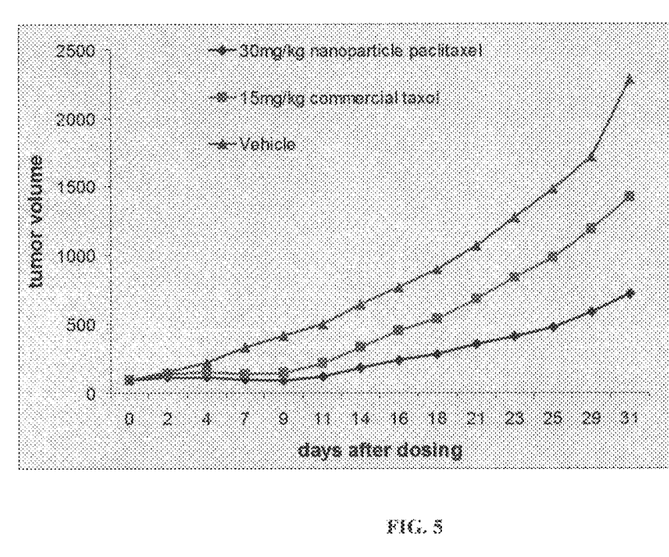
FIG. 5: Comparison of antitumor effect for Taxol treatment and the treatment using substantially ethanol free nanoparticles comprising paclitaxel: PEGylated olive oil.

Thirty female SW mice (from Taconic, 5-6 weeks old) were obtained. Human breast cancer cell line MDA-MB-231 was obtained from American Type Culture Collection (Manassas, Va.). The cells were cultured in 75 $cm^2$ flask containing RPMI-1640 medium supplemented with 10% fetal bovine scrum and incubated at 37° C. in humidified atmosphere of 5% $CO_2$. Cells were allowed to grow until 80-90% confluence and harvested with 0.05% trypsin/0.53 mM EDTA (Gibco) before each subsequent passage. 1*$10^6$ cells were injected in each flank (both sides) of the mice. Mice were ear tagged and randomly assigned to three groups (10 per group: Taxol group, paclitaxel: PEGylated olive oil nanoformulation group and PEGylated olive oil only group). Tumors were allowed to grow. Taxol (15 mg/kg of paclitaxel), paclitaxel: PEGylated olive oil nanoformulation (30 mg/kg of paclitaxel), and PEGylated olive oil alone (3000 mg/kg) was administered intravenously to mice in respective groups for five consecutive days. Mice were monitored for body weight and tumor size measurements daily for three weeks post dosing. Mortality and body weight data are shown in FIG. 3 and FIG. 4, respectively. At the end of the study mice were weighed, euthanized, and gross necropsy was performed. No abnormality was observed. Results obtained for tumor shrinkage are summarized in FIG. 5.

Example 12

Synthesis of Hydroxyl Modified Olive Oil and PEGylated Olive Oil via Oxymercuration-Demercuration Chemistry Olive oil (50 mg), 1,2-ethanediol (200 mg), mercury acetate (300 mg) are dissolved in 25 mL dimethylformamide and reaction mixture is stirred at room temperature for 4 days. The reaction mixture is cooled to 0° C. and sodium borohydride (300 mg) dissolved in 10 ml water is added slowly The reaction mixture is stirred at room temperature for 30 min and saturated with sodium chloride. The reaction mixture is extracted in ether. The organic layer is dried on anhydrous magnesium sulfate, filtered and evaporated under vacuum to obtain hydroxyl modified olive oil. The modified olive oil is dissolved in chloroform. To this, three fold molar excess of $MPEG_{2000}$-isocyanate (Monomethoxy polyethyle glycol 2000-isocyanate) over that of the modified olive oil is added. Dibutyltin dilaurate (10 mg) is added and reaction mixture stirred at 50° C. overnight. The reaction mixture is poured in excess of hexane to precipitate the product PEGylated olive oil. Schematic representation of the synthesis is shown in FIG. 6

Example 13

Figure 7:
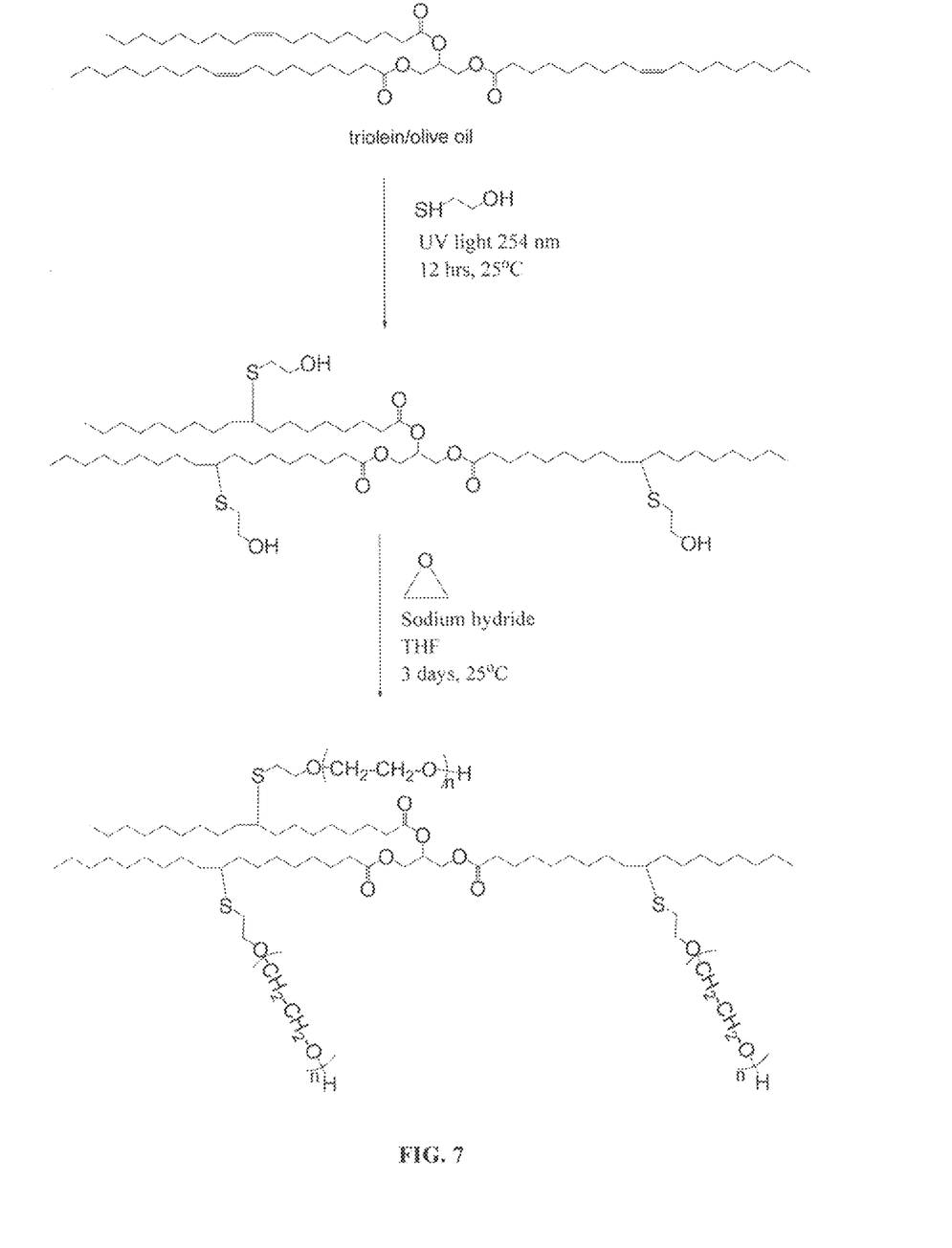
FIG. 7: Schematic representation of synthesis of PEGylated triolein/PEGylated olive oil as safer substitute excipient to Cremophor EL via alternate, ethylene oxide polymerization chemistry.

Synthesis of Hydroxyl Modified Triolein and PEGylated Triolein via Ethylene Oxide Polymerization Triolein (500 mg, 0.56 mmol) is taken in a glass vial. To this, 2-mercaptoethanol (0.55 mL, 6.6 mmol) and 2,2,-dimethoxyphenyl acetophenone (29 mg, 0.11 mmol) are added. The mixture is mixed with a disposable Pasteur pipette and the vial is irradiated overnight through the walls with a hand-held ultraviolet lamp ($UV_{max}$=254 nm). Saturation of double bonds in triolein by addition of 2-mercaptoethanol is confirmed by $^1H$ NMR. The adduct of triolein-2-mercaptoethanol (hydroxyl-modified triolein) is purified on a $C_{18}$ plug by loading the sample directly onto the plug and eluting with water until all excess unreacted 2-mercaptoethanol is removed. Hydroxyl-modified triolein is eluted with 9:1 dichloromethane: methanol. Hydroxyl-modified triolein (100 mg) is dissolved in 10 mL tetrahydrofuran in a round bottom flask. To this, 20 mg sodium hydride is added and stirred under Argon for 30 min. To this, 1 g cooled, liquid ethylene oxide is added via syringe and reaction mixture is stirred at room temperature for 3 days. The reaction mixture is concentrated in vacuum to obtain PEGylated triolein. Schematic representation of the synthesis is shown in FIG. 7.

Example 14

Synthesis of Thiol Modified Ethyl Oleate and its Conjugate with Poly(Methacryloyloxyethylphosphoryl Choline) by Chain Transfer Polymerization Ethyl oleate (Sigma-Aldrich, 3.1 g, 10 mmol) is taken in a glass vial. To this, 1,2-ethanedithiol (Sigma-Aldrich, 5.6 mL, 66 mmol) and 2,2,-dimethoxyphenyl acetophenone (Sigma-Aldrich, 290 mg, 11 mmol) is added. The mixture is mixed with a disposable Pasteur pipette and the vial is irradiated overnight through the walls with a hand-held ultraviolet lump ($UV_{max}$=254 nm). Saturation of double bonds in ethyl oleate by addition of 1,2-ethanedithiol is confirmed by $^1H$ NMR. The adduct of ethyl oleate-1,2-ethanedithiol (thiol modified ethyl oleate) is purified to remove excess of 1,2-ethanedithiol by loading reaction mixture on a $C_{18}$ plug directly and cluting with water until all excess 1,2-ethanedithiol is removed. Thiol modified triolein free from polymerized byproducts (if any), is eluted using 9:1 dichloromethane: methanol. The solvents are evaporated under reduced pressure to obtain clear, colorless oil. Unpolymerized state of thiol modified ethyl oleate is confirmed by 1H NMR spectroscopy.

Figure 8:
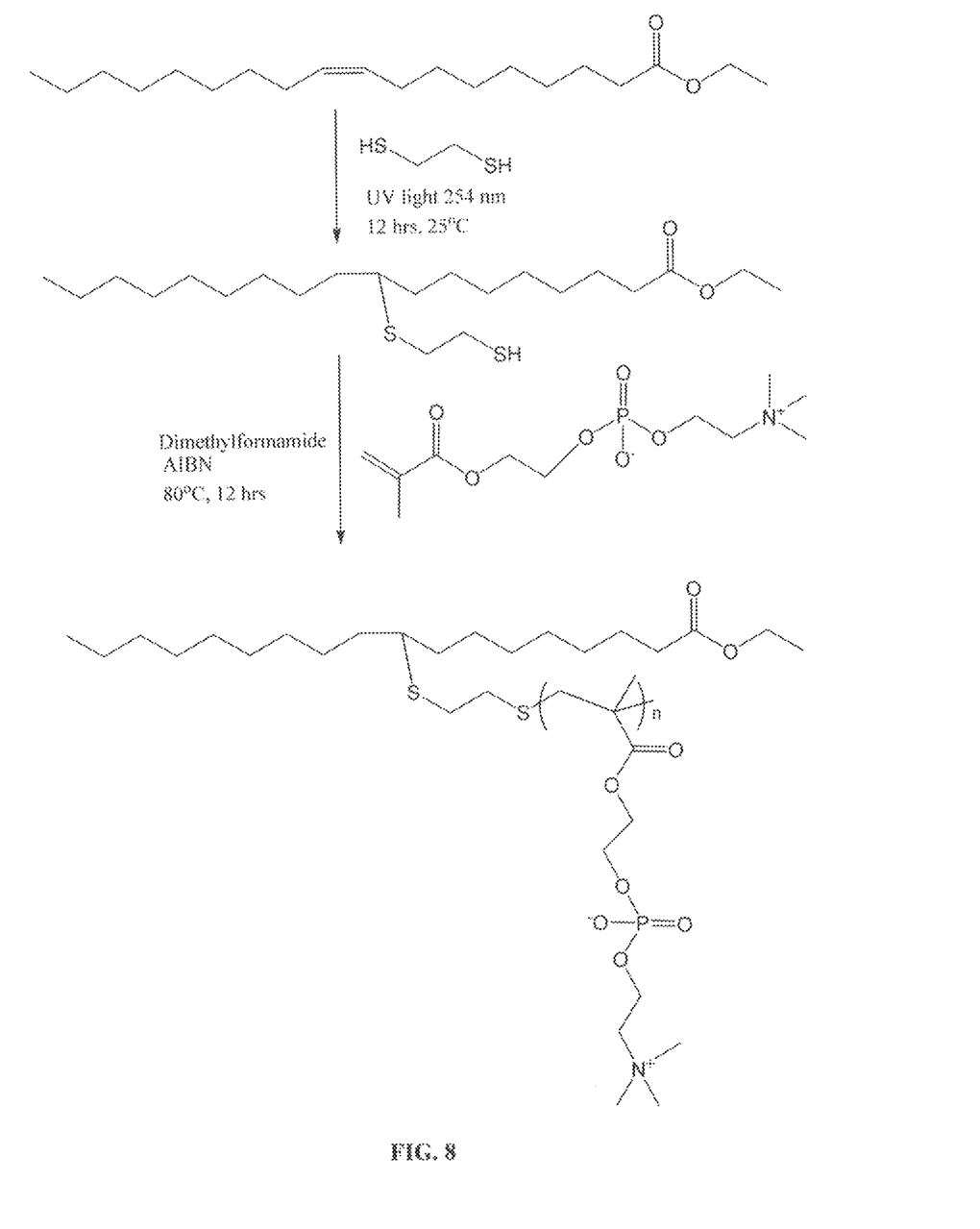
FIG. 8: Schematic representation of synthesis of conjugate of ethyl oleate and poly(2-methacryloyloxyethylphosphoryl choline) via chain transfer polymerization chemistry.

A 250 mL three neck round bottom flask is charged with stir bar, thiol modified ethyl oleate (404 mg, 1 mmol), methacryloyloxyethylphosphoryl choline (2.95 g, 10 mmol, from Sigma-Aldrich). azobisisobutyronitile (16.4 mg, 0.1 mmol), and dimethylformamide (100 mL). The reaction mixture is purged with nitrogen for 30 min at room temperature. Nitrogen purging is continued and the flask is immersed in oil bath preheated to 80° C. to initiate chain transfer polymerization of methacryloyloxyethylphosphoryl choline. The reaction mixture is stirred under nitrogen purging at 80° C. for 12 hrs. The reaction mixture is cooled to room temperature and poured in 1000 mL diethyl ether to precipitate the product—conjugate of thiol modified ethyl oleate and poly(methacryloyloxyethylphosphoryl choline). Schematic representation of the synthesis is shown in FIG. 8.

Example 16

Conjugate of Hydroxyl Modified Olive Oil and Poly(Methoxylpolyethylene Glycol-Methacrylate) Via Atom Transfer Radical Polymerization In a 250 mL round bottom flask equipped with magnetic stir bar, hydroxyl modified olive of Example 12 (1.071 g, 1 mmol), trimethylamine (0.5 g, 4.34 mmol) are dissolved in 100 mL dichloromethane. The flask is kept in an ice bath and stirred magnetically. To this, 2-bromoisobutyryl chloride (0.69 g, 3 mmol) in 10 mL dichloromethane is added slowly and reaction mixture is stirred for 3 hrs at 0° C. followed by 12 hrs at room temperature. The reaction mixture is washed with 200 mL water three times and organic layer is dried on anhydrous sulfate. The reaction product i.e. Atom Transfer Radical Polymerization initiator-modified olive oil is isolated by flash chromatography.

Figure 9:
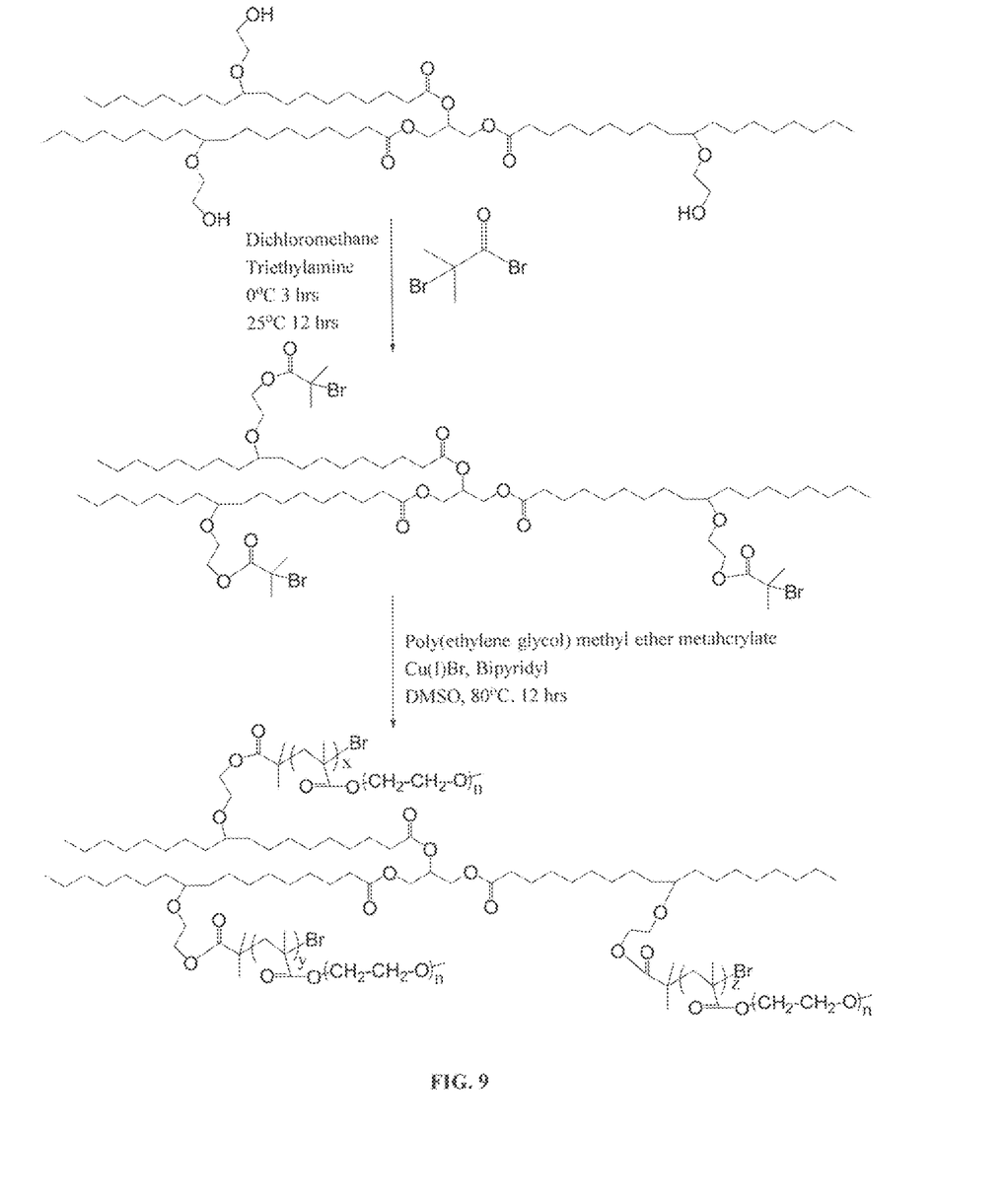
FIG. 9: Schematic representation of synthesis of conjugate of triolein/olive oil and poly(methoxypolyethylene glycol-methacrylate) via atom transfer radical polymerization chemistry.

Atom Transfer Radical Polymerization initiator-modified olive oil (1.5 g, 1 mmol), poly(ethylene glycol)methyl ether methacrylate (9.50 g, 10 mmol (Mn=950)), and 100 mL dimethylsulfoxide are added in a round bottom flask equipped with magnetic stir bar. The mixture is stirred magnetically to obtain clear solution. The solution is purged with nitrogen for 30 min at room temperature. To this, Copper (I) bromide (0.143 g, 1 mmol) and 2,2'-bipyridyl (0.312 g, 2 mmol) are added to initiate polymerization of poly(ethylene glycol)methyl ether methacrylate and the flask is immersed in oil bath preheated to 80° C. Stirring is continued under nitrogen purging for 12 hrs. The reaction mixture is cooled to room temperature. Copper salts are removed by passing the reaction mixture over a silica gel column. The colorless solution is poured in cold diethyl ether to separate conjugate of hydroxyl modified olive oil and poly(methoxylpolyethylene glycol-methacrylate) which is further purified by dia-filtration. Schematic representation of the synthesis is shown in FIG. 9.

TABLE 1

Stability of substantially ethanol free nanoparticles comprising paclitaxel and PEGylated olive oil

| PEGylated olive oil w/w (%) | Paclitaxel w/w (%) | Stability (days) |
|---|---|---|
| 99 | 1 | >7* |
| 98 | 2 | 3 |
| 97 | 3 | 1 |

*Study was discontinued after 7 days when precipitation was not observed

TABLE 2

Hypersensitivity and tolerability study

| Taxol arm | | | Paclitaxel: PEGylated olive oil arm | | |
|---|---|---|---|---|---|
| Subgroup | Mortality | HSR | Subgroup | Mortality | HSR |
| 15 mg/kg | 0 | Y | — | — | — |
| 30 mg/Kg | 1/5 on day 5 | Y | 30 mg/Kg | 0 | N |
| 40 mg/Kg | 3/5 immediately, 2 on day 4 | Y | 40 mg/Kg | 1/5 on day 11 | N |
| 50 mg/Kg | 5/5 immediately | Y | 50 mg/Kg | 2/5 on day 8, 1 on day 11 | N |

HSR = Hypersensitivity reaction
Y = HSR started within 20 minutes of dosing: Shivering, sniffing, shortness of breath, hunched posture, lethargy, and convulsions. Gradual recovery in 6 hrs
N = None of the observations made in Y above.

The invention claimed is:
1. A method of treating breast cancer consisting intravenously administering to a subject in need thereof a therapeutically effective amount of substantially ethanol free nanoparticle composition wherein nanoparticle composition consists nanoparticles having hydrodynamic diameter of 10 to 200 nm consisting 1 to 10 percent by weight of a taxane and 90 to 99 percent by weight of a substantially hydroxyl free unsaturated oil saturated at least at one site of unsaturation by a covalently attached hydrogen atom and a covalently attached water soluble polymer of formula wherein n is an integer selected from 2 to 12,
X is thiol reactive linker containing functionalities selected from a group consisting maleimido, acrylate, methacrylate, isocyanate, isothiocyanate, iodoacetamido, bromoacetamido, sulfovinyl, thioether,
POLY is substantially biocompatible water soluble polymer selected from a group consisting polyethylene glycol, polyethylene oxide, polyethylene glycol methyl ether, homo and heterobifunctional polyethylene glycols, polyethylene glycol-co-polypropylene glycol, polyethylene oxide-block-polypropylene oxide, polyethylene glycol-acrylate, polyethylene glycol-methacrylate, methoxypolyethylene glycol-acrylate, methoxypolyethylene glycol-methacrylate, poly(polyethyleneglycol-metahcrylate)s, poly(methoxypolyethyleneglycol-methacrylate)s, poly(N-2-hydroxypropyl-methacrylamide), poly(N-vinylpyrrolidone), poly(N-isopropylacrylamide), poly(acrylic acid), poly(methacrylic acid), poly(2-aminoethyl methacrylate), poly(N,N-dimethylaminoethyl methacrylate), poly(2-methacryloyloxyethylphosphorylcholine) and combinations thereof,
substantially hydroxyl free unsaturated oil is oil selected from a group of edible oils consisting olive oil, corn oil, canola oil, soybean oil, rapeseed oil, linseed oil, trilinolein, triolein, peanut oil, sunflower oil, mustard oil, almond oil, palm oil, sesame oil, safflower oil, cottonseed oil, grape seed oil, rice bran oil, mono, di, triglycerides of unsaturated fatty acids of C7 to C22 chain length, unsaturated fatty acids of C7 to C22 chain length, and mixtures thereof,
and taxane is selected from a group consisting paclitaxel, docetaxel, cabazitaxel.

* * * * *